(12) United States Patent
Lapalme

(10) Patent No.: US 12,219,899 B2
(45) Date of Patent: Feb. 11, 2025

(54) MULTIFUNCTIONAL SYSTEM FOR ADAPTABLE HARVESTING

(71) Applicant: SAMI AGTECH INC., Varennes (CA)

(72) Inventor: Eric Lapalme, Varennes (CA)

(73) Assignee: SAMI AGTECH INC., Varennes (CA)

( * ) Notice: Subject to any disclaimer, the term of this patent is extended or adjusted under 35 U.S.C. 154(b) by 830 days.

(21) Appl. No.: 17/295,925

(22) PCT Filed: Dec. 9, 2019

(86) PCT No.: PCT/CA2019/051769
§ 371 (c)(1),
(2) Date: May 21, 2021

(87) PCT Pub. No.: WO2020/118419
PCT Pub. Date: Jun. 18, 2020

(65) Prior Publication Data
US 2022/0007582 A1 Jan. 13, 2022

Related U.S. Application Data

(60) Provisional application No. 62/777,483, filed on Dec. 10, 2018.

(51) Int. Cl.
*A01D 46/30* (2006.01)
*A01D 91/04* (2006.01)
(Continued)

(52) U.S. Cl.
CPC ............ *A01D 46/30* (2013.01); *A01D 91/04* (2013.01); *B65G 61/00* (2013.01); *G01N 21/27* (2013.01);
(Continued)

(58) Field of Classification Search
CPC .............................. A01D 46/30; A01D 91/04
See application file for complete search history.

(56) References Cited

U.S. PATENT DOCUMENTS 3,768,239 A  10/1973  Staats et al.
4,015,366 A   4/1977  Hall
(Continued)

FOREIGN PATENT DOCUMENTS

CN   103481296 A   1/2014
EP      1112679 A3  7/2001
(Continued)

OTHER PUBLICATIONS

European Search report, Nicolai Sebastien, Aug. 4, 2022, 11 pages.

*Primary Examiner* — Abigail A Risic
(74) *Attorney, Agent, or Firm* — Fasken Martineau DuMoulin LLP; Johann Gest; Dennis Haszko

(57) ABSTRACT

There is provided a system, installed on a vehicle or trailer, for performing an agricultural task. The system comprises a platform connecting to the vehicle or trailer and comprising a socket for an accessory. A plurality of accessories is provided, wherein one accessory is selected among them for installation in the accessory socket. A vision system is operatively connected to a computer and collects data of the environment about the accessory, the computer using the collected data to determine an instruction for performing the agricultural task and to send the instruction to the accessory installed in the accessory socket to perform the agricultural task. The accessory is interchangeable in the accessory socket depending on the agricultural task. The box handling stage and pallet mounting stage can be robotized for efficient automation.

19 Claims, 8 Drawing Sheets

(51) Int. Cl.
*B65G 61/00* (2006.01)
*G01N 21/27* (2006.01)
*G01N 33/02* (2006.01)
*H04N 23/90* (2023.01)

(52) U.S. Cl.
CPC .... *G01N 33/025* (2013.01); *B65G 2201/0211* (2013.01); *H04N 23/90* (2023.01)

(56) References Cited

U.S. PATENT DOCUMENTS

| | | | |
|---|---|---|---|
| 4,482,960 | A | 11/1984 | Pryor |
| 4,532,757 | A | 8/1985 | Tutle |
| 4,655,667 | A | 4/1987 | Plumb et al. |
| 4,718,223 | A | 1/1988 | Suzuki et al. |
| 4,843,561 | A | 6/1989 | Larson |
| 5,220,775 | A | 6/1993 | Vogel et al. |
| 5,544,474 | A | 8/1996 | Finkelstein |
| 6,886,445 | B2 | 5/2005 | Adams |
| 7,765,780 | B2 | 8/2010 | Koselka et al. |
| 8,276,739 | B2 | 10/2012 | Bastian, II et al. |
| 9,315,324 | B2 | 4/2016 | Salazar, III |
| 9,475,189 | B2 | 10/2016 | Kahani |
| 9,914,601 | B2 | 3/2018 | Morency et al. |
| 9,995,524 | B2 * | 6/2018 | Sigety .................. F25D 17/067 |
| 2005/0246056 | A1 | 11/2005 | Marks et al. |
| 2006/0213167 | A1 | 9/2006 | Koselka et al. |
| 2011/0047951 | A1 * | 3/2011 | Moore .................. A01D 46/24 |
| | | | 56/328.1 |
| 2013/0204437 | A1 * | 8/2013 | Koselka ................. A01D 91/00 |
| | | | 701/25 |
| 2014/0345304 | A1 * | 11/2014 | Leung .................... F25D 17/06 |
| | | | 62/380 |
| 2016/0309650 | A1 | 10/2016 | Jens et al. |
| 2017/0113592 | A1 | 4/2017 | Dagorret |
| 2017/0227969 | A1 | 8/2017 | Murray et al. |
| 2017/0265392 | A1 | 9/2017 | Van de Vegte et al. |
| 2017/0280620 | A1 | 10/2017 | Desai et al. |
| 2018/0092304 | A1 * | 4/2018 | Moore ................... B25J 9/0084 |
| 2019/0261565 | A1 * | 8/2019 | Robertson .............. A01D 46/22 |
| 2020/0041193 | A1 * | 2/2020 | Sigety .................... F25D 17/06 |
| 2020/0281122 | A1 * | 9/2020 | Mor ........................ A01F 15/00 |
| 2020/0323140 | A1 * | 10/2020 | Gielis .................... A01D 46/24 |
| 2021/0243967 | A1 * | 8/2021 | Bartrom .................. A01G 3/08 |
| 2021/0368687 | A1 * | 12/2021 | Wisdom ............... G06V 20/188 |
| 2021/0374894 | A1 * | 12/2021 | Wisdom ................. G06V 20/56 |
| 2024/0147903 | A1 * | 5/2024 | Wisdom ................ A01D 46/30 |

FOREIGN PATENT DOCUMENTS

| | | |
|---|---|---|
| EP | 2086308 B1 | 1/2011 |
| EP | 3258772 A1 | 12/2017 |
| EP | 3347707 A1 | 7/2018 |
| WO | 2006063314 | 6/2006 |
| WO | 2016133918 A1 | 8/2016 |
| WO | 2017044484 A1 | 3/2017 |
| WO | 2018015416 | 1/2018 |
| WO | 2018087546 A1 | 5/2018 |
| WO | 2018115832 A1 | 6/2018 |

* cited by examiner

US 12,219,899 B2

MULTIFUNCTIONAL SYSTEM FOR ADAPTABLE HARVESTING

CROSS-REFERENCE TO RELATED APPLICATIONS

This application claims the priority or benefit of U.S. provisional patent application 62/777,483, filed Dec. 10, 2018, the specification of which is hereby incorporated herein by reference in its entirety.

BACKGROUND

(a) Field

The subject matter disclosed generally relates to harvesting systems. More specifically, it relates a robotic system for harvesting produce.

(b) Related Prior Art

Harvesting is known to be a labor-intensive operation, involving a large number of workers, working simultaneously in the field to harvest produce, moving along with a tractor and trailer to gather the harvested fruits and vegetables. This work, shown in exemplary FIG. 1, can be physically hard, and is often performed under intense sunlight. Adding the fact that the work is mostly seasonal makes it hard to hire staff and provide interesting working conditions.

As a result, many systems for automating harvesting of produce were developed in order to reduce the required workforce. For example, automated systems have been described which can pick oranges in trees, and other systems have similarly been developed for other types of produce.

SUMMARY

According to an aspect of the invention, there is provided a system for performing an agricultural task, the system being installed on a vehicle or trailer and comprising:
  a platform connecting to the vehicle or trailer and comprising a socket for an accessory;
  a plurality of accessories, wherein one accessory is selected among the plurality of accessories for installation in the accessory socket;
  a computer for processing data; and
  a vision system which is operatively connected to the computer and which collects data of the environment about the accessory, the computer using the collected data to determine an instruction for performing the agricultural task and to send the instruction to the accessory installed in the accessory socket to perform the agricultural task,
  wherein the accessory is interchangeable in the accessory socket depending on the agricultural task.

According to an embodiment, the platform comprising the socket is a lateral extension which extends laterally from the vehicle or trailer.

According to an embodiment, there is further provided, opposing said lateral extension, a second lateral extension which extends laterally from the vehicle or trailer on another side thereof.

According to an embodiment, the plurality of accessories all have a portion thereof which fits with the socket for interchangeable installation therein.

According to an embodiment, the plurality of accessories comprises a plurality of different robotic arms.

According to an embodiment, the vision system comprises a color camera and the collected data of the environment comprise spectral data on vegetal objects undergoing the agricultural tasks.

According to an embodiment, the vision system comprises at least two cameras positioned side-by-side and the collected data of the environment comprises tridimensional data on vegetal objects undergoing the agricultural tasks.

According to an embodiment, there is further provided a conveyor extending between the accessory socket and the vehicle or trailer for receiving vegetal objects and translating the vegetal objects toward the vehicle or trailer.

According to an embodiment, there is further provided, at an end of the conveyor on the vehicle or trailer, a box filling stage comprising a robotic arm for picking the vegetal objects from the conveyor and placing the vegetal objects in a box.

According to an embodiment, there is further provided a pallet mounting stage comprising a box handling arm for displacing a completed box from the box filing stage onto the pallet mounting stage, the pallet mounting stage comprising a stage for placing the completed box and a wrap applicator, the wrap applicator performing a relative revolution movement around said stage for wrapping the completed box onto a pallet.

According to an embodiment, there is further provided a pallet conveyor for evacuating the pallet from the pallet mounting stage.

According to an embodiment, there is further provided a storage trailer receiving the pallet evacuated from the pallet conveyor, the storage trailer comprising an entry at a front thereof and having sides thereof being closed.

According to an embodiment, the storage trailer is refrigerated and is removably attached as an additional trailer from the vehicle or trailer.

According to an aspect of the invention, there is provided a method for performing an agricultural task, with a system installed on a vehicle or trailer and further comprising a socket for receiving an accessory among a plurality of accessories, the method comprising the steps of:
  selecting one accessory among the plurality of accessories and installing the accessory in the accessory socket;
  collecting data of the environment about the accessory using a vision system,
  sending the collected data to a computer for processing;
  by the computer, determining an instruction using the collected data for performing the agricultural task;
  sending the instruction to the accessory installed in the accessory socket, the accessory being thereby operated to perform the agricultural task, and
  once the agricultural task is completed, interchanging the accessory in the accessory socket for another one to perform another agricultural task.

According to an embodiment, collecting data of the environment about the accessory comprises using a color camera to collect spectral data on vegetal objects undergoing the agricultural tasks.

According to an embodiment, collecting data of the environment about the accessory comprises using at least two cameras positioned side-by-side to collect tridimensional data on vegetal objects undergoing the agricultural tasks.

According to an embodiment, there is further provided the step of picking up vegetal objects by the accessories, dropping the vegetal objects onto a conveyor, and conveying the vegetal objects toward the vehicle or trailer.

According to an embodiment, there is further provided the step of picking the vegetal object from the conveyor and placing the vegetal object in a box using a robotic arm.

According to an embodiment, there is further provided the step of using a box handling arm for displacing a completed box onto a stage and automatically spinning said stage while applying a wrap applicator therearound, the wrap applicator further being translated vertically simultaneously for wrapping the completed box onto a pallet.

According to an embodiment, there is further provided the step of evacuating the pallet into a storage trailer from a front thereof using a pallet conveyor, further comprising refrigerating the storage trailer while sides thereof are closed.

According to an embodiment, collecting data of the environment about the accessory comprises determining whether a vegetal object is According to an embodiment, collecting data of the environment about the accessory comprises recording the data along with a geolocation of the vegetal object, the method further comprising predicting a future status of the vegetal object based on the recorded data.

According to an embodiment, determining whether the vegetal object is ready to be picked up or not comprises estimating a weight, a volume or a quality grade of the vegetal object.

According to an embodiment, there is further provided the step of picking the vegetal object by the accessory and dropping the vegetal object onto the system.

According to an embodiment, there is further provided the step of providing a plurality of available boxes and continuously or periodically recording existing contents of the plurality of boxes.

According to an embodiment, there is further provided the step of using a sorting camera for sorting the vegetal object dropped onto the system, and using a robotic arm distinct from the accessory, picking up the vegetal object and dropping the vegetal object in a box, among the plurality of available boxes, to performing a sorting which corresponds to the weight, the volume or the quality grade as estimated, wherein the sorting is made repeatedly in view of the recorded existing contents of the plurality of boxes.

According to an embodiment, providing the socket comprises providing at least two sockets for receiving simultaneously at least two different types of accessories among a plurality of accessories, each type of accessories dedicated to a different type of vegetal object.

According to an embodiment, there is further provided the step of using a sorting camera for sorting the vegetal object dropped onto the system, and using a robotic arm distinct from the accessory, picking up the vegetal object and dropping the vegetal object in a box, among the plurality of available boxes, to perform a sorting which corresponds to the type of vegetal object.

According to an embodiment, collecting data of the environment about the accessory comprises using a preliminary camera for spotting a presence of a vegetal object and a fine camera system for aiding in the step of determining the instruction for performing the agricultural task by collecting data with a finer precision that the preliminary camera to determine precise movements of the accessory.

As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

It was found that the systems described in the prior art as automated systems for harvesting produce lack versatility. Systems are not adaptable to be used for a great variety of fruits or vegetables. They are normally intended to pick a specific type of fruit or vegetable.

Figure 1:
FIG. 1 is a picture illustrating manual harvesting, according to the prior art.
Figure 2:
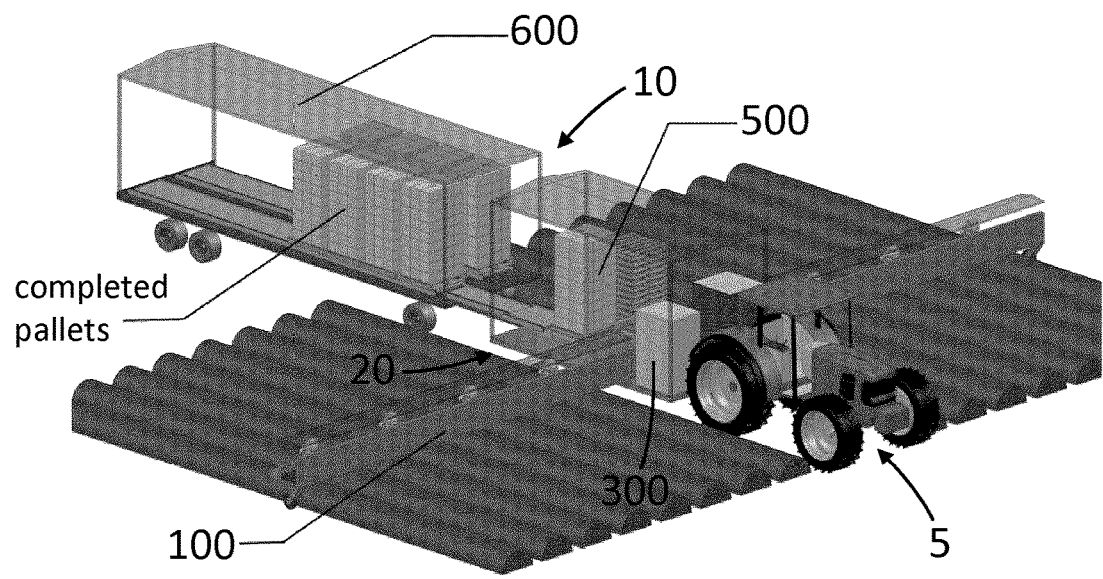
FIGS. 2, 3 and 4 are two perspective views and a top view of a multifunctional system for adaptable harvesting, according to an embodiment of the invention.
Figure 3:
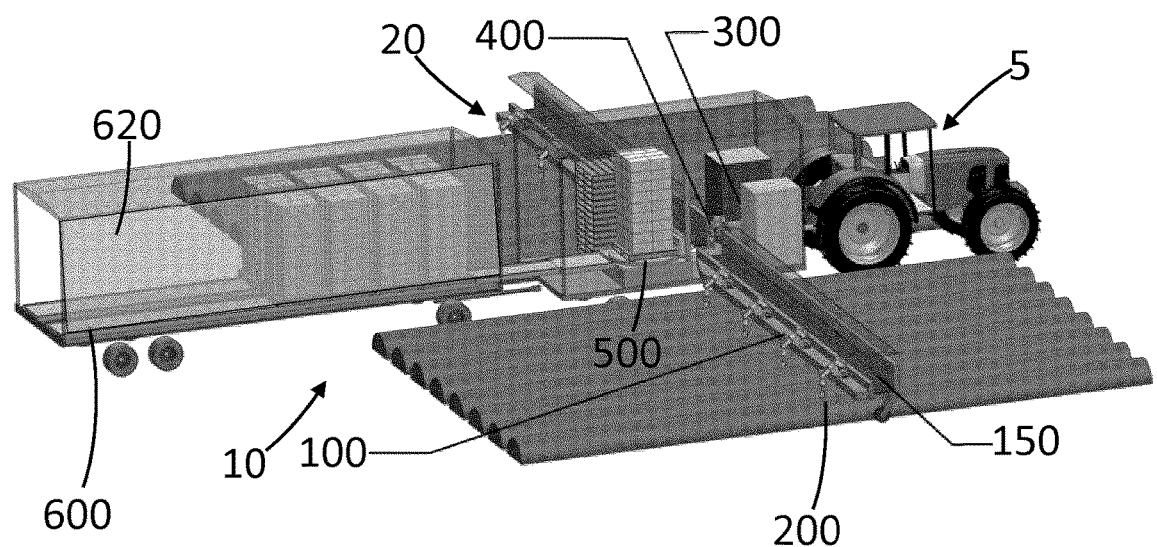
Figure 4:
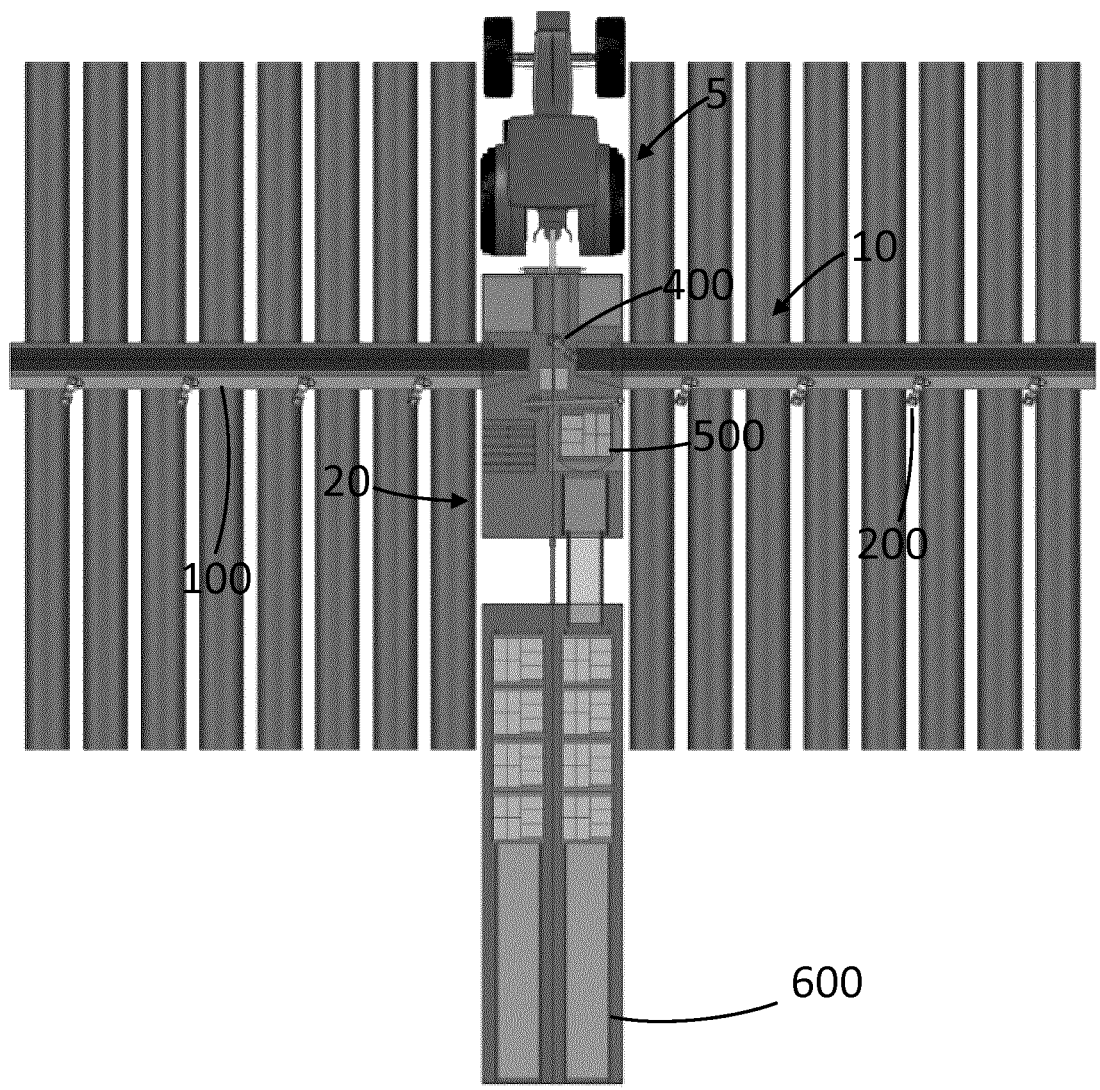

As shown in FIGS. 2, 3 and 4, there is described a system 10 for harvesting produce which is multifunctional as it can be adapted to perform a variety of agricultural tasks in a field, including an adaptable system for selectively and interchangeably mounting a selection of apparatuses among a variety thereof, which ensures versatility of the system 10 in terms of the types of plants, fruits or vegetables (or more generally, vegetal objects) which can be harvested, and also in terms of associated non-picking tasks that can be performed simultaneously by the same system, such as making measurements with sensors at the local level, i.e., in-situ, right above the plant.

The system 10 is a system working in cooperation with a vehicle 5, such as a tractor, or on a portion of a vehicle or a trailer 20 being a part of the vehicle 5 or being attached thereto. In other words, the system 10 can be mounted on a trailer hooked on the vehicle 5, or a trailer integrated to the vehicle 5, and the trailer 20 should include both types of trailers (separate from the vehicle 5 or forming a part thereof). In most cases, the system would be mounted on a dedicated, custom trailer 20 (either permanently integrated to the vehicle or attached thereto in a removable fashion), acting as a support for other equipment discussed herein below.

The system 10 comprises lateral extensions 100 which extend laterally and horizontally away from the trailer 20. While there can be only one lateral extension 100, drawings show that the lateral extensions 100 are provided as a pair on both lateral sides of the trailer 20, as shown in FIGS. 2-4. The lateral extension 100 acts as an arm which has a length to extend laterally away from the vehicle from said length, thereby covering a plurality of rows in the field. When the vehicle moves forward, the extension of the lateral extension 100 implies that a surface of the field will be covered as the vehicle is displaced. Providing two lateral extensions 100 implies that a larger surface will be covered, but providing a single lateral extension 100 may make the system 10 easier to handle in the field, especially if the vehicle makes frequent turns and if there are trees, buildings or other obstacles nearby.

Figure 6:
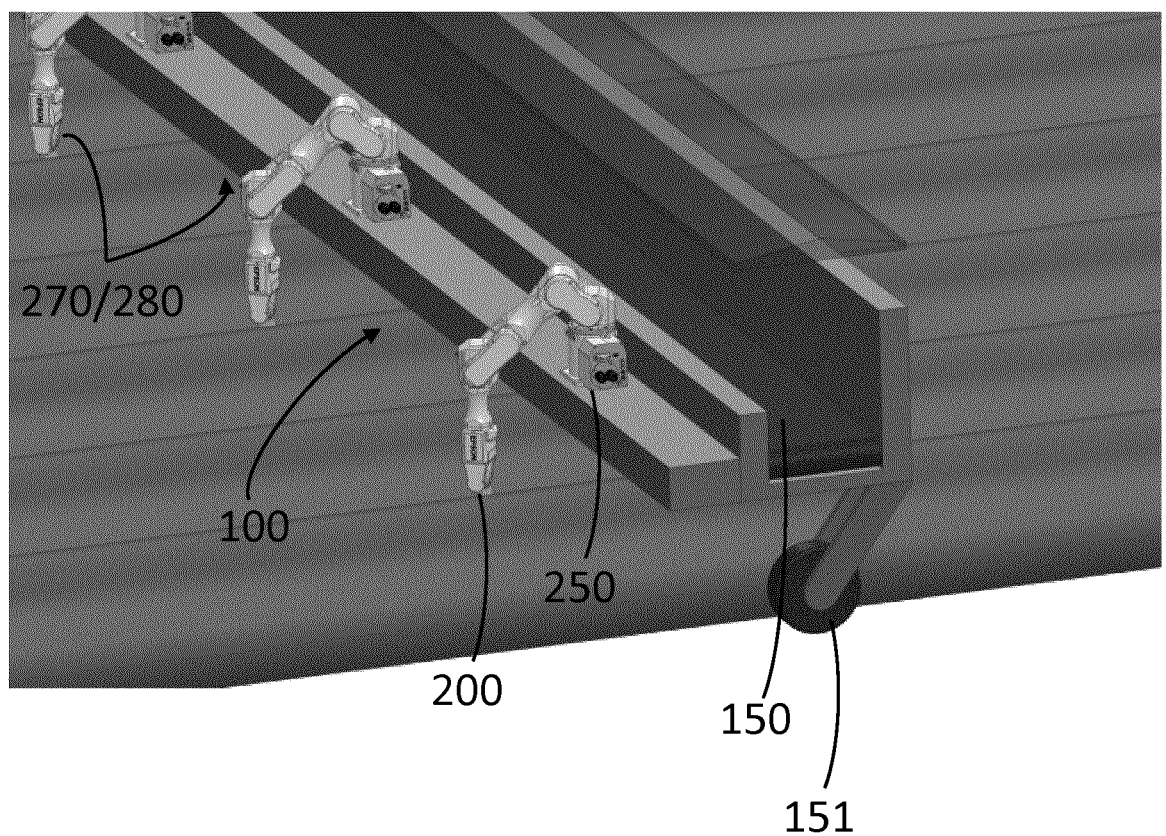
FIG. 6 is a close-up perspective view of the system showing in greater detail the accessories on a lateral extension comprising a conveyor, according to an embodiment of the invention.

The lateral extensions 100 each act as a platform which comprise accessory sockets 250, onto which accessories 200 are installed, as shown in FIG. 6. The accessories 200 are removable from the sockets 250 to be interchanged if or when needed. For example, one of the possible accessories 200 should include robotic picking hands which are manipulated in an automated manner according to particular instructions (discussed further below). The accessory sockets 250 are each used as a mechanical connector for mechanically installing and supporting an accessory 200, and the mechanical connector should fit a plurality of different accessories 200, by having a particular shape, while each of the accessories 200 has a complementary shape. The accessories 200 do not necessarily need to have the same exact shape, but should all comprise a portion which, in a way or another, complements the shape of the socket 250 to fit therein. Optionally, a mechanical adapter, or coupler, can be provided as an additional device in-between for mechanically coupling an accessory 200 to the socket 250 if the shape does not fit.

The lateral extensions 100 extend long enough to cover a substantial length on a field, i.e., a plurality of rows, as mentioned above and as shown in FIGS. 2-4. The height of the lateral extensions 100 should be adapted to the length of the accessories 200 and to the height of the vegetation in the field, e.g., about 1 meter high.

Each one of the lateral extensions 100 (or the single one) forms a platform which includes a conveyor 150. The conveyor 150 is used to receive produce picked by the accessories 200 and displace the received produce to the trailer 20 where they are treated. The accessories 200 should be able to reach the produce to handle when being installed in the accessory sockets 250 on the lateral extensions 100. Therefore, at least one of the accessories 200 and the lateral extensions 100 should be adjustable in height. This can be performed by ensuring the accessory 200 is long and articulatable, and/or by having the lateral extensions 100 at an adjustable height using a height adjusting mechanism of any suitable type (hydraulic cylinders, electric motor, engine, jack, etc.).

According to an embodiment, a stabilizing wheel 151 can be added under the distal end of a lateral extension 100 (or close thereto) to support a part of the weight thereof and improve height stability of the lateral extension 100. The stabilizing wheel 151 may be connected or cooperate with to the height adjusting mechanism mentioned above, if there is provided such a mechanism. For example, if the mechanical connection of the lateral extension 100 with the trailer acts as the height adjusting mechanism (e.g., actuator, chain, engine of some sort, etc.), then the stabilizing wheel 151 should have a height that changes accordingly, either by using a spring or by providing a similar mechanism within the stabilizing wheel 151 driven by instructions that ensure coherent movement. Alternatively, the stabilizing wheel 151 may act as the height adjusting mechanism, while the mechanical connection of the lateral extension 100 with the trailer undergoes a passive translation by being free to translate upwardly.

As mentioned above, the accessories 200 can be interchanged on the accessory sockets 250 depending on the task to be performed. The accessories 200 can be either wired to a connector on the socket 250, or have a wireless connection, for communication with a computer 300. Moreover, the accessories 200 can be either wired to an electrical connector on the socket 250, or have a battery, for receiving the power required to perform the tasks.

Preferably, the socket 250 comprises an electrical contact connected to a power source within the vehicle (or within the trailer, or within the lateral extension 100). Accordingly, the accessories 200, in the portion thereof to be fitted into the socket 250, should comprise a cooperating electrical contact to receive electrical power from the electrical contact of the socket 250. The electrical power is then converted within each accessory to perform the desired task, typically a mechanical movement, or a measurement.

In an alternative or complementary embodiment, the socket 250 comprises a source of mechanical energy, such as a rotating gear within the socket 250 which is fed with power from elsewhere in the vehicle and individually controlled in the socket 250. In this case, the accessories 200, in the portion thereof to be fitted into the socket 250, should comprise a cooperating gear to receive the mechanical power from the socket 250, converted using other gears or adapters to drive the mechanical parts of the accessories 200.

Accessories 200 can be fixed on the lateral extension 100. In another embodiment, a rail can be provided and the sockets can move on the rail to reach a desired position. This particular embodiment is useful to adapt to a defective apparatus, or in the case of a very expensive apparatus being used for which there is only one apparatus, which therefore needs to be translated to perform its task alone on the lateral extension 100. The rail can be manual, such that the socket 250 comprising an accessory 200 can be moved to a desired location and fixed there. Otherwise, the rail can be powered and the sockets 250 can be translated in an automated manner.

The accessories 200 should receive instructions from the computer 300 to be operated in an automated manner. They should also collect data and send the collected data to the computer 300, either directly (wirelessly, e.g., using Bluetooth™ technology, WiFi™ technology, etc.), or indirectly by being distributed to or through the sockets toward the central computer 300 using wire cables or wireless technology from the sockets 250 or any other intermediate device. Preferably, the computer 300 is in-situ, for example on the trailer 20.

Other sensors 280 can be provided on the lateral extensions or elsewhere on the trailer to send data to the computer 300. Examples of such sensors 280 can include a temperature sensor, a humidity sensor, a chemical sensor for measuring soil contents in phosphate and various nitrogen compounds, etc. These types of sensors are mentioned herein because they have utility in agronomy.

Figure 5:
FIG. 5 is a picture illustrating a task to be performed by the system, according to an embodiment of the invention.

According to an embodiment, there is provided a vision system 270 which is used to view the produce to be harvested or identified in the field. An example of a viewing task is shown in FIG. 5, which is a picture showing an item to be grabbed (i.e., a mature vegetable), other items to be identified, but not ready to be grabbed yet, and other elements such as leaves, stems and soil. The vision system 270 should transmit images to the computer 300 for proper identification of all these elements. The vision system 270 may acquire and transmit optical data in the wavelength spectrum which is suitable for the task.

The vision system 270 is in communication (either wired or wireless as in the other examples mentioned above) and can be provided as a plurality of devices installed on a bottom portion of the lateral extension(s) 100, and/or on the accessories 200 or the accessory sockets 250.

According to a more specific embodiment, the vision system 270 includes two types of camera, which can include: 1) a three-dimensional camera system (which by itself should comprise at least two cameras having their own, distinct viewpoints distant from a predetermined distance in order to determine a three-dimensional localization of objects and shape in the environment); and 2) a color camera, which specializes in getting wavelength information from the light received on the sensor to determine color with high precision.

The 3D camera system is useful to understand the exact location and shape of objects in the environment. The information is extracted by having the computer 300 analyze received images and determine, using computer vision algorithms, the 3D arrangements of elements in the images. In practice, in a field, this would include determining that an object is an item to be harvested (either immediately or later), its location, its extension in space (i.e., its shape), and further identifying obstacles therearound, such as leaves.

The color camera is useful to contribute in the identification of the item to be harvested, e.g., identifying that it is a fruit or vegetable, identifying what it is (i.e., the fruit or vegetables species or variety) and determining a level of maturity of the fruit or vegetable. This can be helpful to identify if a fruit or vegetable is ripe or corresponds to what is being harvested.

In particular, some wavelengths bands may be more useful than others for viewing particularities of some plants and not for other plants; or some wavelengths bands may be more useful to detect stages of plant growth while others are more adapted to detect illnesses. Therefore, the vision system 270 may include cameras having a very broad band of wavelengths being monitored, or it includes cameras which have different complementary (or overlapping) bands of wavelengths. Typically, the range of visible wavelengths should be covered, and infrared is also useful for a variety of tasks.

In addition to the vision system 270, a geolocation system can be used advantageously. The geolocation system can be, for example, a GPS system which determines with a high accuracy the location of the system 10 in the field. Since the position of each accessory 200 on the system 10 is known, the exact location of a given item to be later harvested can be recorded and the system therefore remembers that such an item is found in the field at a precise location. The geolocation system can be included in the sensors 280, or elsewhere, such as within the accessories 200, within the sockets 250, within the computer 300, or elsewhere in the system 10. Geolocation systems other than a GPS system can be used, for example a radio system using fixed references in the field, with their own geolocation, with the radio system that monitors the exact distance of the system from these fixed references.

According to an embodiment, lights can be provided on the lateral extensions and/or on the apparatus or by the apparatus socket. Lights can ensure that darker areas in the field, for example in the shadow of the leaves, are sufficiently lit such that the color and shapes can be properly identified, as described above.

An advantage of using lights in combination with the vision system 270 include the ability to perform night harvesting. Since the system is automated, the presence of light at the level of the apparatuses is sufficient to allow night harvesting. At night, produce are not subject to intense sunlight, which can damage their skin, so picking them up at night does not make them subject to this intense sunlight. Moreover, at night, fruits and vegetables have higher water content than during the day, which makes them heavier. Therefore, less items are necessary to fill a box above a predetermined weight threshold. Furthermore, they can have a more appealing look for a consumer.

As mentioned above, each of the accessory sockets 250 can advantageously receive one apparatus selected among a plurality of accessories 200, each to be used for a specific task or group of tasks.

According to an embodiment, each accessory can be used with a selection of produce to be harvested. The accessories can resemble the typical accessory which would normally be operated manually by a person harvesting the produce in the field. For example, if a field comprising asparaguses is being harvested, the apparatus sockets 250 should be equipped with accessories adapted to the harvest of asparaguses, comprising for example a cutter or scissors to cut a base of the asparagus, and a hand comprising a minimum number of fingers (or an annular prehension member) to grip the asparagus being cut and then displace the cut asparagus toward the conveyor 150, onto which it is released. The accessory 200 is then instructed to deploy back toward the field for detecting and harvesting a next occurrence of asparagus in the field.

In order to ensure that each apparatus is adapted to perform a specific task, which also needs to be consistent with how the information collected by the vision system 270 is analyzed and with eventual instructions to the sorting robot arm 450 (described further below in relation with the sorting of harvested produce in the vehicle), the computer 300 should have a program to implement all operations and instruct all peripherals accordingly. According to an embodiment, the computer 300 has a software product installed thereon which is adapted to receive additional software programs to be installed as add-ons. These add-ons can be downloaded on the computer 300 to enable it to perform new tasks in combination with new or existing accessories. Doing so allows the system to be usable with only a subset of the accessories and their corresponding operating software. Individual programs, designed for specific tasks, can be added, corrected or improved individually.

Figure 7:
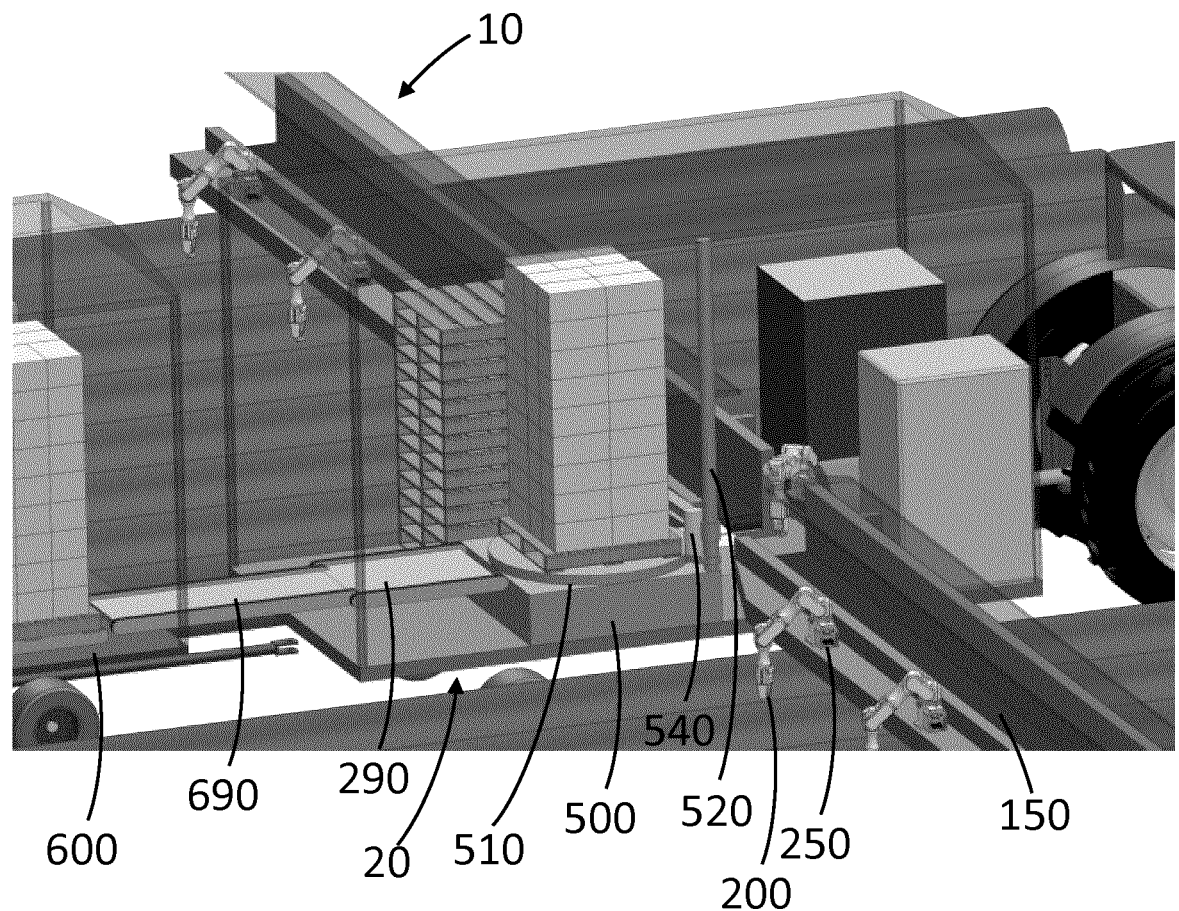
FIGS. 7 and 8 are a close-up perspective view and a top view of the system showing in greater detail the box filling stage and the pallet mounting stage, according to an embodiment of the invention.
Figure 8:
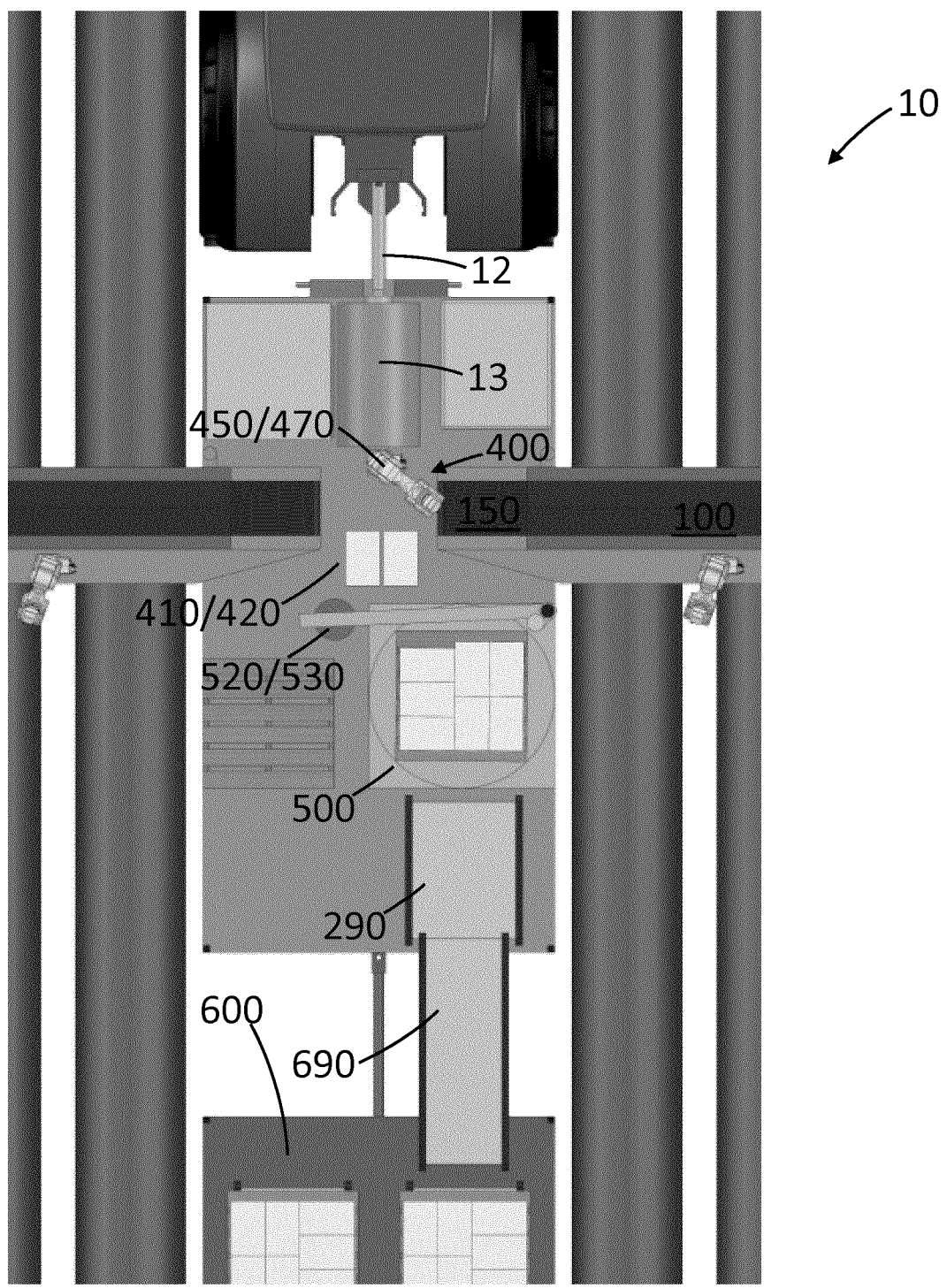

Now referring to FIGS. 7-8, according to an embodiment, the trailer 20 comprises a box filling stage 400 which is located at a location in the trailer which corresponds to the reception area of the conveyor 150 of the lateral extension 100. If there are two lateral extensions 100, they are normally provided on each side by that reception area such that the box filling stage 400 is located between the proximal ends of both lateral extensions 100. The box filling stage 400 comprises a surface area 410 adapted to receive at least one box, or preferably a plurality of boxes, to receive the produce delivered by the conveyors at their proximal end at the reception area on the trailer 20.

According to an embodiment, the box filling stage 400 comprises a weight measurement apparatus 420 which measures in real time (i.e., continuously, or periodically) the weight of the at least one box on the surface area 410. The weight measurement apparatus 420 can communicate with the computer 300 to send the acquired data for processing by the computer 300. The weight measurement apparatus 420 can be provided for each spot which receives a box on the surface area 410, to weigh each box independently or individually, or for the whole surface area 410, in which case the weight measurement apparatus 420 measures the weight of all boxes and their contents together. Since the produce is added individually into the boxes, the computer 300 can monitor the individual weight of each box and its own contents by simply measuring the total weight and recording the box in which each item is added or which box is removed from the box filling stage 400.

According to an embodiment, there is provided a sorting robot arm 450 which is adapted to grab the produce received from a conveyor 150, displace it and release it in a box, preferably an appropriate one of the plurality of boxes.

The sorting robot arm 450 comprises a sorting camera 470 which monitors the incoming produce in terms or identity and properties of the produce and location in space. The sorting robot arm 450 can communicate with the computer 300 to send the acquired data for processing by the computer 300. The computer 300 can then send back instructions to the sorting robot arm 450 to act on the produce.

In a simple embodiment, sorting robot arm 450 can be instructed to move its distal end to grab the item arriving at the trailer 20; the instructions should include some prediction of the trajectories of both the item and the sorting arm 450 such that they can meet and the item be grabbed. The sorting arm 450 is then instructed to move itself and the item such that the item is displaced above a box or within the box (the lower the better to avoid damaging the produce) and the item is then released inside the box. The weight measurement apparatus 420 measures the weight of the box, and when detected to reach or exceed a predetermined threshold, the box is released or displaced, for example to a pallet mounting stage 500 as described below, and is replaced by a new, empty box.

In a more sophisticated embodiment, there are provided a plurality of boxes simultaneously on the stage, and the sorting robot arm 450 can be instructed, based on the produce being grabbed and analyzed by the sorting camera 470, to release the produce in a specific one of the plurality of boxes. For example, the sorting camera 470, in combination with the computer 300 with which it communicates, can determine a quality of the produce being handled, based on visible properties such as size (volume), color or shape, and instruct the sorting arm to release the produce in one of the boxes corresponding to its quality grade. The same can apply in a case where the system 10 is used in a field with a variety of different types of produce, in which case the produce being handled will be classified in the box corresponding to its own identity.

In another embodiment, the computer 300 receiving data from the sorting camera 470 and the weight measurement apparatus 420 can determine how much weight of produce still needs to be released in each box to reach its threshold, and determine which box should be the one receiving a current item being handled to optimize the weight of each box and avoid exceeding the nominal weight of the box. For example, if boxes are sold at a price corresponding to nominal weight of 20 pounds per box, it is expected that each box weighs at least 20 pounds; in a field being harvested in typical conditions, workers would simply put produce in the box until it is filled, knowing the nominal weight has been exceeded. This can result in boxes containing more fruit or vegetable than expected, and the result is that produce are given away as a bonus to the acquirer. Using the current system 10, each item being handled can be weighed prior to release, and the weight of each box is known. If one box has a weight of 19.6 pounds and another one has a weight of 19.2 pounds, and if the produce being handled has a measured weight of 0.9 pound, the system 10 will attribute the produce to the box for which the weight excess will be minimized (e.g., the one weighing 19.2 pounds), and weight for a lighter item to be put in the first box which is already closer to its target threshold, thus optimizing the number of boxes that meet the contractual conditions of a nominal weight. The sorting arm 450 can have its own weight measurement apparatus or implement other weighing technique in order to evaluate the weight of an item being handled.

According to an embodiment, the box filling stage 400 comprises a box mounting apparatus, which comprises an arm (such as the sorting robot arm 450, as shown, or any suitable robotized or automated arm other than the sorting robot arm 450 shown in FIG. 8) for picking a new folded box, open it using fingers, and displace it to its appropriate spot on the surface area 410 where it can receive incoming produce while being continuously or periodically monitored for its contents (such as being weighed).

Still referring to FIGS. 7-8, according to an embodiment, the trailer 20 comprises a pallet mounting stage 500 which is located on another area in the trailer 20, for example, just behind the area on which the box filling stage 400 is located. As shown in these figures, some room can be made for additional empty pallets to be used when a given pallet is completed and pushed back for storing.

According to an embodiment, the pallet mounting stage 500 comprises a pallet receiving surface 510, which can take the form of a rotating stage having a surface on which a pallet is provided. A support 520, such as a vertically-extending pole, can be provided close to this pallet receiving surface 510, and supports a box handling arm 530. The box handling arm 530 is responsible for grabbing the completed box on the box filling stage 400, as instructed by the computer 300 with which it communicates, and displaces this box onto the pallet or onto boxes already packed thereon, thus contributing in completing the pallet with boxes.

According to an embodiment, once the pallet is complete, i.e., its height reaches a threshold, or when a row is complete, the pallet receiving surface 510 is rotated (i.e., it can spin around its own central axis using a dedicated mechanism or motor), while a wrap applicator is applied onto the box row(s) of the completed pallet. The wrap applicator 540 can be installed on the support 520, and is a device which applies a layer of plastic wrapping sheet (or any other equivalent thereof) onto the row(s) of boxes. Normally, the wrapping applicator 540 would be located at a bottom of the pallet and start the application of the layer of plastic wrapping sheet while the whole pallet is being spun (by spinning the pallet receiving surface 510, resulting in a relative revolution of the wrap applicator 540 around the pallet being wrapped); the wrapping applicator 540 slowly moves upwardly at the same time (i.e., simultaneous vertical translation) up to the last row at the top of the completed pallet, in which case the whole completed pallet is wrapped and secured.

According to an embodiment, there is further provided a storage trailer 600. The storage trailer 600 should be adapted to receive pallets or boxes for storage during the operation of the system. For example, the storage trailer 600 can be removably attached at the rear end of the trailer 20.

According to an exemplary embodiment, a chain conveyor 690 can be provided on a floor surface of the trailer 20 to displace pallets or boxes from the pallet mounting stage 500 (or from the box filling stage 400 if there are no pallets involved) toward the rear end of the trailer 600. Similarly, a chain conveyor 690 can be provided on a floor surface of the storage trailer 600 to displace pallets or boxes from a front end toward the rear end thereof, preferably from a rear location of the pallet mounting stage 500. Both chain conveyors (290, 690) should be aligned and approximately at the same height such that pallets or boxes can be displaced substantially seamlessly from one to the other. Since a vehicle (including trailers) are usually about twice as large as a pellet, there are provided two chain conveyors inside each trailer, both extending parallel to each other and substantially spaced apart, such that each one can lead to one row (right or left) in the storage trailer 600. The pallets being sequentially brought thereinto should be distributed to the left or right to avoid misbalancing the storage trailer 600.

According to an embodiment, the storage trailer 600 can comprise lateral walls 620 (or side walls). The lateral walls 620, shown on one side of the storage trailer 600 in FIG. 3, are normally absent from any storage trailer used in the industry, since boxes or pallets are normally manually loaded laterally, i.e., from the sides, which must be left completely open. With the proposed form of loading using the chain conveyors (290, 690), such manual loading can be avoided. Lateral walls 620 can therefore be added, along with a rear door, and the front opening, though which the chain conveyors (290, 690) operate, can be advantageously provided with rubber curtains. These additions to the trailer, currently inapplicable in a field trailer during typical harvesting operations, can be used to refrigerate the storage trailer 600. A refrigeration assembly can thus be added to the storage trailer 600 to perform this task. Together, the walls, insulation and refrigeration assembly can maintain a lower temperature of the completed pallets while the trailer (in this case, the storage trailer 600) is still in the field, during the harvesting process. Back doors for the storage trailer 600 can allow back unloading onto an unloading deck.

The system 10 described above can advantageously be powered by the power take-off (PTO) 12 of the vehicle (e.g., tractor), coupled with an electric generator 13 which feeds electric power to the conveyors, apparatuses, computer, box filling stage, pallet mounting stage, sockets and accessories, etc. Mechanical parts such as the conveyor 150 can also be powered by a mechanical coupling with the PTO.

According to an exemplary embodiment, the computer 300 may communicate with the vehicle's onboard system or with specific contacts in the vehicle to adjust the vehicle's speed in the field based on the current workload, or a near-future estimation thereof.

According to an embodiment, the vision system 270 comprises different sets of cameras as described above, e.g., a three-dimensional camera and a color camera. According to a more specific embodiment, one of the camera types can be located on a bottom portion of the lateral extensions 100 and act as a preliminary spotter for the produce. The other type of camera can be located on the accessories 200 and have a finer degree of vision. For example, if the preliminary camera system does not identify anything to come, the accessory 200 can stay in standby, thus saving energy and computer processing power. It can be awakened if this preliminary camera system spots an interesting object, or if a location is reached in which an almost ripe fruit or vegetable was spotted in the previous days (thus requiring recording the status of previously spotted fruit and vegetable, and anticipating an updated status thereof for the present day). In this case, the fine camera system on the accessories 200 will wake up from standby mode to detect more precise properties of an upcoming item.

As mentioned above, sensors 290 are integrated into the system 10. Advantageously, these sensors 290 can implement a "Supervisory Control And Data Acquisition" (SCADA). Data are transmitted to the computer 300 which can itself be connected to the internet for uploading data to a remote server. The computer 300 can also query data from remote servers, such as weather data.

As described above, the accessories 200 can be adapted to dispense pesticide to the plants in a very localized manner, i.e., at the plant level. By collecting weather forecast information, the computer 300 can instruct the system 10 to avoid dispensing a pesticide (or dispense less of it) if rain is forecasted in the near future (in which case it would simply be drained away by rainwater).

According to an embodiment, the accessories 200 selected to be installed into the sockets 250 can be different from one socket to the other, or the system 10 can be operated repeatedly by changing the apparatuses between each iteration. Operating the system 10 in this way allows harvesting a field in which the produce are diverse and variable from plant to plant, as in a home garden. More precisely, such fields do not exist or a large scale at this time due to a too great complexity for maintaining or harvesting. As can be understood from the description above, the system 10 is able to identify each item at an individual level in the field, and therefore, the system 10 may be used in a field comprising a variety of different types of produce within the same row. This would have to include rows in the field, and further avoids the need for crop rotation, while reducing risks of insect issues or epidemics.

The system 10 may further be used to plant the plants in the field in any desired pattern. In fact, it can be used for a variety of tasks in addition to harvesting.

For example, the system 10 can be used for sowing. The box filling stage 400 described above can be replaced by a seed container, and the conveyors can be operated in reverse, such that the apparatuses can grab seeds on the conveyor and dispose them onto the field. By using an appropriate accessory, the seeding operation can be a seeding under a film of plastic or fabric, since an appropriate accessory or combination of accessories would at the same time have a tool to temporarily push away the film, plant the seed, and bring the film back over the soil.

Similarly, the system 10 can plant small plants in the soil, in which case the seeds are replaced by a small plant. The system 10 may advantageously record the exact location where it was planted. If a variety of fruits or vegetables are planted, the system may tag each planting operation to record the exact location and the identity of what is planted there, which would help in easily localizing and identifying produce during harvesting or pesticide application. Thereafter, the system may repeatedly record the status of the previously planted/seeded plant, thereby monitoring the growth thereof and appearance of fruit/vegetable thereon. Afterwards, using such status records similar records from other similar plants, it can anticipate an updated status thereof for the present day based on the past measurements.

As mentioned above, a small quantity of pesticide can be added in-situ to the plant, preferably depending on forecasted or current weather conditions, and also depending on prior pesticide additions to avoid any excess.

According to an embodiment, the color camera mentioned above may collect color information to be analyzed by the computer 300 to identify the presence of insects. Pesticides can be dispensed accordingly.

According to an embodiment, insect presence in the field is determined by the computer 300 and is sent to a remote server for archiving. The accumulated information can be used to identify insect spreading in a given region and act accordingly, i.e., destroy a crop which would be a source of insect or disease spreading in view of regional winds, which normally drive regional insect migration.

The system 10 can also identify unripe fruits or vegetables and predict time of harvest, Since the system 10 can be operated every day, the overall harvest production can be estimated for the next days, thus helping the operator to better estimate crop yield for the next days and plan deliveries accordingly.

For example, using color to assess maturity, the system 10 can identify which item is ready to be picked up in one day, two days, three days, etc., with an optional uncertainty for those which are ready in more than two days.

Moreover, similar tasks can be performed for specific produce which require flagging prior to harvest. For example, cauliflowers need to be picked up five days after turning white. Typical harvesting involves placing a rubber band around each cauliflower indicating the date at which it will need to be harvested. The current system 10 is able to install such an identifier and, more advantageously, can simply record the exact location of the individual item and pick it up after the predefined number of days (e.g., 5 days for the cauliflower having turned white) by simply recognizing its very presence on this exact location, without having to use a physical indicator such as a rubber band.

The exact location of a fruit or vegetable can also be correlated with the initial seeding or planting, which can be geolocated, especially if the field is seeded with a variety of produce.

According to an embodiment, the vision system 270 can identify exceeding plant stems, especially those that bear no fruit, and cut these stems using an accessory comprising a cutter or scissors, to avoid these stems to grew uselessly and divert plant nutrients and resources from the fruit.

Other operations such as weeding can also be performed, in a similar fashion, i.e., various agricultural tasks can be performed.

Over a significant period of time, the recorded measurements made on the field on a high number of produce and at high frequency (temperature, humidity, soil composition, measured pesticide applications, follow-up of the leaves and produce color, etc.), along with the fact that the produce may have been characterized in terms of weight, shape and color when harvesting, allows the system 10 to collect big data which can be used to improve agronomy or simply statistics of crop yields in correlation with various factors.

Figure 9:
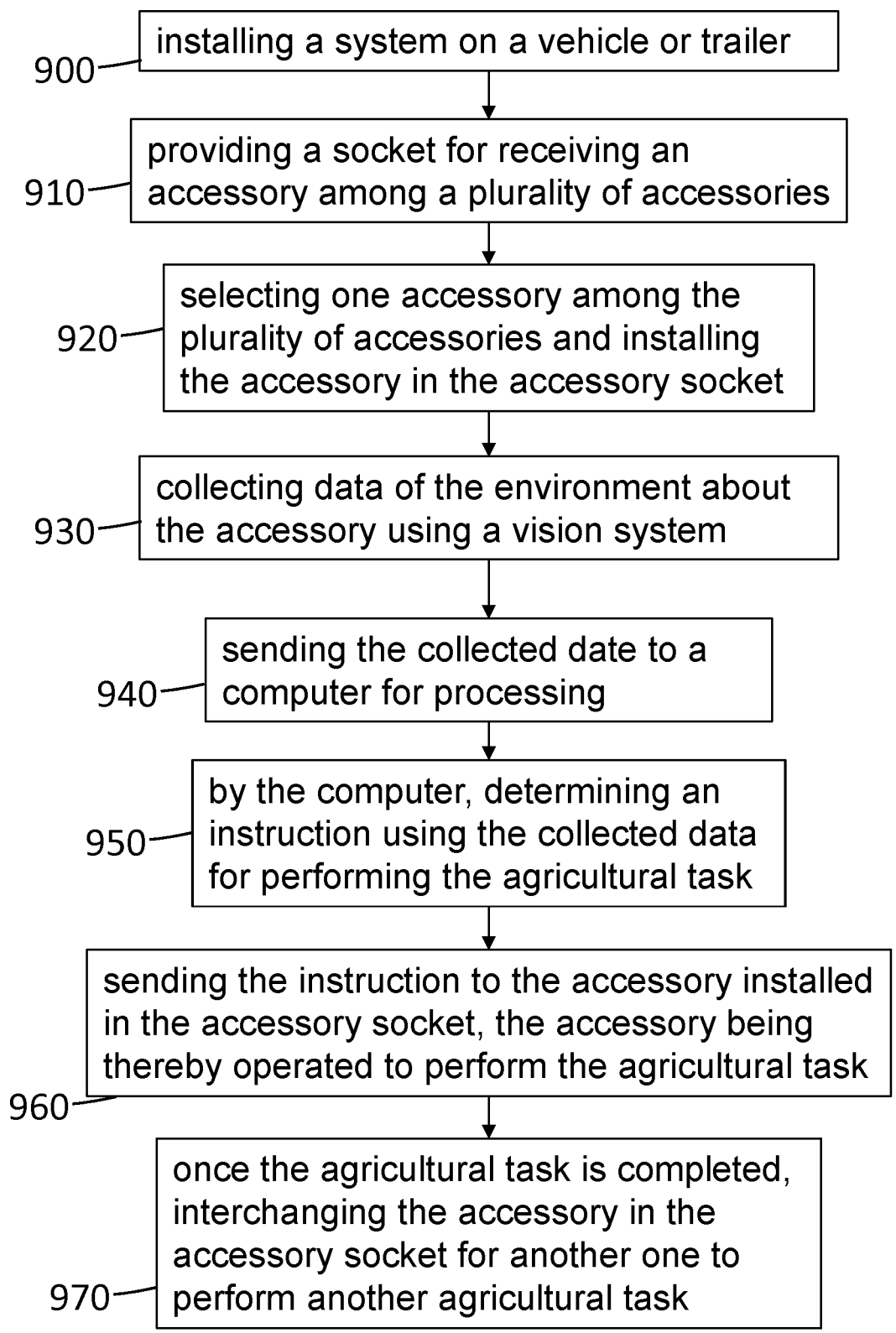
FIG. 9 is a flowchart illustrating a method for adaptable harvesting, according to an embodiment of the invention.

FIG. 9 shows a method for performing an agricultural task, the method comprising the steps of:
Step 900: installing a system on a vehicle or trailer,
Step 910: providing a socket for receiving an accessory among a plurality of accessories;
Step 920: selecting one accessory among the plurality of accessories and installing the accessory in the accessory socket;
Step 930: collecting data of the environment about the accessory using a vision system,
Step 940: sending the collected date to a computer for processing;
Step 950: by the computer, determining an instruction using the collected data for performing the agricultural task;
Step 960: sending the instruction to the accessory installed in the accessory socket, the accessory being thereby operated to perform the agricultural task, and
Step 970: once the agricultural task is completed, interchanging the accessory in the accessory socket for another one to perform another agricultural task.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A system for performing an agricultural task, the system being mountable to a vehicle or portion of a vehicle or trailer and comprising:
   a platform for connecting to the vehicle or trailer or portion of a vehicle and comprising an accessory socket for an accessory;
   a plurality of accessories, wherein one accessory is selected among the plurality of accessories for installation in the accessory socket;
   a computer for processing data; and
   a vision system operatively connected to the computer and configured for collecting data of an environment about the accessory, the computer being configured for using the collected data to determine an instruction for performing the agricultural task and to send the instruction to the accessory installed in the accessory socket to perform the agricultural task, and
   wherein the accessory is interchangeable in the accessory socket depending on the agricultural task,
   wherein the system further comprises a conveyor extending between the accessory socket and a reception area of the system for receiving and translating vegetal objects between the accessory and the reception area, and
   wherein the system further comprises an automated stage operable about the reception area and configured for at least one post-processing task selected from box loading, weighing, sorting and monitoring the vegetable objects received from the conveyor.

2. The system of claim 1, wherein the platform comprising the accessory socket is a lateral extension which extends laterally from the vehicle or trailer.

3. The system of claim 1, wherein the plurality of accessories all have a portion thereof which fits with the accessory socket for interchangeable installation therein.

4. The system of claim 1, wherein the vision system comprises a color camera and the collected data of the environment comprise spectral data on vegetal objects undergoing the agricultural tasks.

5. The system of claim 4, wherein the vision system comprises at least two cameras positioned side-by-side and the collected data of the environment comprises tridimensional data on vegetal objects undergoing the agricultural tasks.

6. The system of claim 1, further comprising at an end of the conveyor on the vehicle or trailer, a box filling stage comprising a robotic arm for picking the vegetal objects from the conveyor and placing the vegetal object in a box, and
   further comprising a pallet mounting stage comprising a box handling arm for displacing a completed box from the box filing stage onto the pallet mounting stage, the pallet mounting stage comprising a stage for placing the completed box and a wrap applicator, the wrap applicator performing a relative revolution movement around said stage for wrapping the completed box onto a pallet.

7. The system of claim 6, further comprising a pallet conveyor for evacuating the pallet from the pallet mounting stage, further comprising a storage trailer receiving the pallet evacuated from the pallet conveyor, the storage trailer comprising an entry at a front thereof and having sides thereof being closed, wherein the storage trailer is refrigerated and is removably attached as an additional trailer from the vehicle or trailer.

8. A method for performing an agricultural task, with a system mountable to a vehicle or portion of a vehicle or trailer and further comprising an accessory socket for receiving an accessory among a plurality of accessories, the system further comprising a conveyor extending between the accessory socket and a reception area of the system for receiving and translating vegetal objects between the accessory and the reception area, the system further comprising an automated stage operable about the reception area, the method comprising:
   selecting one accessory among the plurality of accessories and installing the accessory in the accessory socket;
   collecting data of an environment about the accessory using a vision system,
   sending the collected data to a computer for processing;
   by the computer, determining an instruction using the collected data for performing the agricultural task;
   sending the instruction to the accessory installed in the accessory socket, the accessory being thereby operated to perform the agricultural task,
   operating the automated stage to perform at least one post-processing task selected from box loading, weighing, sorting and monitoring the vegetal objects received from the conveyor; and
   once the agricultural task is completed, interchanging the accessory in the accessory socket for another one to perform another agricultural task.

9. The method of claim 8, wherein said collecting the data of the environment about the accessory comprises using a color camera to collect spectral data on vegetal objects undergoing the agricultural tasks.

10. The method of claim 9, wherein said collecting the data of the environment about the accessory comprises using at least two cameras positioned side-by-side to collect tridimensional data on vegetal objects undergoing the agricultural tasks.

11. The method of claim 8, further comprising picking up vegetal objects by the accessories, dropping the vegetal objects onto a conveyor, and conveying the vegetal objects toward the vehicle or trailer, and picking the vegetal object from the conveyor and placing the vegetal object in a box.

12. The method of claim 11, further comprising using a box handling arm for displacing a completed box onto a stage and automatically spinning said stage while applying a wrap applicator therearound, the wrap applicator further being translated vertically simultaneously for wrapping the completed box onto a pallet, and evacuating the pallet into a storage trailer from a front thereof using a pallet conveyor, and further comprising refrigerating the storage trailer while sides thereof are closed.

13. The method of claim 8, wherein said collecting the data of the environment about the accessory comprises determining whether a vegetal object is ready to be picked up or not by estimating a weight, a volume or a quality grade of the vegetal object, recording the data along with a geolocation of the vegetal object, predicting a future status of the vegetal object based on the recorded data.

14. The method of claim 13, further comprising picking the vegetal object by the accessory and dropping the vegetal object onto the system, and providing a plurality of available boxes and continuously or periodically recording existing contents of the plurality of boxes.

15. The method of claim 14, further comprising using a sorting camera for sorting the vegetal object dropped onto the system, and using a robotic arm distinct from the accessory, picking up the vegetal object and dropping the vegetal object in a box, among the plurality of available boxes, to performing a sorting which corresponds to the weight, the volume or the quality grade as estimated, wherein the sorting is made repeatedly in view of the recorded existing contents of the plurality of boxes.

16. The method of claim 14, wherein the accessory socket comprises at least two sockets for receiving simultaneously at least two different types of accessories among a plurality of accessories, each type of accessories being dedicated to a different type of vegetal object.

17. The method of claim 16, further comprising using a sorting camera for sorting the vegetal object dropped onto the system, and using a given robotic arm distinct from the accessory, picking up the vegetal object and dropping the vegetal object in a box, among the plurality of available boxes, to perform a sorting which corresponds to the type of vegetal object.

18. The method of claim 8, wherein said collecting the data of the environment about the accessory comprises using a preliminary camera for spotting a presence of a vegetal object and a fine camera system for aiding in the step of determining the instruction for performing the agricultural task by collecting data with a precision finer than the preliminary camera to determine precise movements of the accessory.

19. A system for performing an agricultural task, the system being mountable to a vehicle or portion of a vehicle or trailer and comprising:
   a platform for connecting to the vehicle or portion of a vehicle or trailer and comprising an accessory socket for an accessory;
   a plurality of accessories, wherein one accessory is selected among the plurality of accessories for installation in the accessory socket;
   a computer for processing data; and
   a vision system operatively connected to the computer and configured for collecting data of an environment about the accessory, the computer being configured for using the collected data to determine an instruction for performing the agricultural task and to send the instruction to the accessory installed in the accessory socket to perform the agricultural task, and
   wherein the accessory is interchangeable in the accessory socket depending on the agricultural task,
   wherein the system further comprises a conveyor extending between the accessory socket and a reception area of the system for receiving and translating vegetal objects between the accessory and the reception area, the conveyor being reversibly operable, and
   wherein the agricultural task comprises at least one of a seeding, sowing, grabbing, recording and planting the vegetable objects, the accessory being configured to correspondingly seed, sow, grab, record or plant the vegetable objects received from the reception area by the conveyor.

* * * * *